(12) United States Patent
Chung et al.

(10) Patent No.: US 7,297,554 B2
(45) Date of Patent: Nov. 20, 2007

(54) IMMUNOASSAY SYSTEM

(75) Inventors: Roy Chung, Carlsbad, CA (US); June Shozi, Buena Park, CA (US)

(73) Assignee: Microdiagnostics, Inc., Orange, CA (US)

( * ) Notice: Subject to any disclaimer, the term of this patent is extended or adjusted under 35 U.S.C. 154(b) by 553 days.

(21) Appl. No.: 10/695,297

(22) Filed: Oct. 28, 2003

(65) Prior Publication Data
US 2004/0087036 A1 May 6, 2004

Related U.S. Application Data

(63) Continuation-in-part of application No. 09/813,071, filed on Mar. 20, 2001, now abandoned, which is a continuation of application No. 09/295,847, filed on Apr. 21, 1999, now abandoned, which is a continuation of application No. 09/195,309, filed on Nov. 18, 1998, now Pat. No. 6,480,310.

(51) Int. Cl.
G01N 33/52 (2006.01)

(52) U.S. Cl. .................. 436/525; 435/7.1; 435/7.2; 435/7.5; 435/7.93; 435/7.94; 435/174; 435/969; 435/973; 436/518; 436/519; 436/523; 436/524; 436/525; 436/526; 436/533; 436/534; 436/823

(58) Field of Classification Search .......... 435/7.1, 435/7.2, 7.5, 7.93, 7.94, 174, 969, 973; 436/518, 436/519, 523, 524, 525, 526, 533, 534, 823
See application file for complete search history.

(56) References Cited

U.S. PATENT DOCUMENTS

| | | | |
|---|---|---|---|
| 4,134,792 A | 1/1979 | Boguslaski et al. | |
| 4,168,146 A | 9/1979 | Grubb et al. | |
| 4,366,241 A | 12/1982 | Tom | |
| 4,407,943 A | 10/1983 | Cole et al. | |
| 4,517,288 A | 5/1985 | Giegel et al. | |
| 4,857,453 A | 8/1989 | Ullman et al. | |
| 4,859,612 A | 8/1989 | Cole et al. | |
| 4,861,711 A | 8/1989 | Friesen et al. | |
| 5,089,391 A | 2/1992 | Buechler et al. | |
| 5,143,852 A | 9/1992 | Valkirs et al. | |
| 5,202,267 A | 4/1993 | Ditlow et al. | |
| 5,233,042 A | 8/1993 | Buechler | |
| 5,237,057 A | 8/1993 | Buechler | |
| 5,405,784 A * | 4/1995 | Van Hoegaerden | 436/523 |
| 5,468,647 A | 11/1995 | Skold et al. | |
| 5,486,452 A | 1/1996 | Gordon et al. | |
| 5,559,041 A | 9/1996 | Kang et al. | |
| 5,656,448 A | 8/1997 | Kang et al. | |
| 5,656,503 A | 8/1997 | May et al. | |
| 5,691,207 A | 11/1997 | Holtlund et al. | |
| 5,712,172 A | 1/1998 | Huang et al. | |
| 5,714,389 A | 2/1998 | Charlton et al. | |
| 5,728,587 A | 3/1998 | Kang et al. | |
| 5,744,358 A | 4/1998 | Jackowski et al. | |
| 5,766,961 A | 6/1998 | Pawlak et al. | |
| 5,770,460 A | 6/1998 | Pawlak et al. | |
| 5,981,298 A * | 11/1999 | Chudzik et al. | 436/514 |
| 6,974,704 B2 * | 12/2005 | Nelson et al. | 436/173 |

FOREIGN PATENT DOCUMENTS

WO  WO 88/08534  11/1988

OTHER PUBLICATIONS

The American Heritage Dictionary. 1976. p. 106.*
Triage Panel for Drugs of Abuse—Directions for Use, Biosite Diagnostics of San Diego, CA (1991) (11 pages).
Thomas Ciesiolka & Hans-Joachim Gabius, An 8-10 Fold Enhancement in Sensitivity for Quantification of Proteins by Modified Application of Colloidal Gold: in Analytical Biochemistry 168, 280-283 (Academic Press, Inc. 1988).
Jan H.W. Leuvering, et al., "A Homogeneous Sol Particle Immunoassay for Human Chronic Gonadotrophin Using Monoclonal Antobodies" in Journal of Immunological Methods 60, 9-23 (Elsevier Science Publishers 1983).
G. Frens, "Controlled Nucleation for the Regulation of the Particle Size in Monodisperse Gold Suspensions" in Nature Physical Science, vol. 241 (Jan. 1, 1973).
U.R. Chakraborty, et al., "An immunogold assay system for the detection of antigen or antibody" in Ann. Biol. Clin. 48, 403-408 (1990).
Lars-Inge Larsson, "Simultaneous ultrastructural demonstration of multiple peptides in endocrine cells by a novel immunocytochemical method" in Nature vol. 282, 743-746 (Dec. 13, 1979).
W. Baschong, et al., " 'Thiocyanate gold': small (2-3 nm) colloidal gold for affinity cytochemical labeling in electron microscopy" in Histochemistry 83:409-411 (Springer-Verlag 1985).
Jan W. Slot, et al., "A new method of preparing gold probes for multiple-labeling cytochemistry" in European Journal of Cell Biology 38, 87-93 (1985).
Christa M. Stoscheck, "Protein Assay Sensitive at Nanogram Levels" in Analytical Biochemistry 160, 301-305 (1987).

(Continued)

Primary Examiner—Bao-Thuy L. Nguyen
(74) Attorney, Agent, or Firm—Stetina Brunda Garred & Brucker

(57) ABSTRACT

A competitive immunoassay, dye and method for rapidly detecting the presence of one or more target ligands within a fluid sample suspected of containing such ligand or ligands. The immunoassay comprises a protein-binding membrane, a first absorbent pad, a second absorbent pad, and a third absorbent pad. The protein-binding membrane has at least two regions of antibodies bound thereto for detecting dissimilar ligands. The second absorbent pad has formed therein a colloidal gold tracer having one, and preferably two or more ligand analog protein complexes adhering thereto. To utilize the system, the immunoassay strip is placed within a fluid sample. To the extent the target ligand is absent, a visual indicator will be provided signaling such absence. To the extent the target ligand is present at or above a threshold level, no such visual signal will be produced.

10 Claims, 2 Drawing Sheets

OTHER PUBLICATIONS

Claudio N. Beristain, et al., "Evaluation of a Dipstick Method for the Detection of Human Immunodeficiency Virus Infection" in Journal of Clinical Laboratory Analysis 9:347-350 (1995).

Jose M. Coco Martin, et al., "Characterization of Antibody Labelled Colloidal Gold Particles and Their Applicability in a Sol Particle Immuno Assay (SPIA)" in Journal of Immunoassay, 11(1), 31-47 (1990).

Jan H.W. Leuvering, et al., "Sol Particle Immunoassay (SPIA)" in Journal of Immunoassay, 1(1), 77-91 (1980).

J. Roth, The Colloidal Gold Marker System for Light and Electron Microscopic Cytochemistry (Academic Press 1993).

Julian E. Beesley, Colloidal Gold: A New Perspective for Cytochemical Marking, (Oxford Univ. Press/Royal Microscopical Society 1989).

Marc Moeremans, et al., "Sensitive Colloidal Metal (Gold or Silver) Staining of Protein Blots on Nitrocellulose Membranes" in Analytical Biochemistry 145, 315-321 (1985).

Jan H.W. Leuvering, et al., "A Sol Particle Agglutination Assay for Human Chorionic Gonadotrophin" in Journal of Immunological Methods, 45, 183-194 (Elsevier/North-Holland Biomedical Press (1981).

William D. Geoghegan and G. Adolph Ackerman, "Adsorption of Horseradish Peroxidase, Ovomucold and Anti-Immunoglobulin to Colloidal Gold for the Indirect Detection of Concanavalin A, Wheat Germ Agglutnin and Goat Anti-Human Immunoglobulin G on Cell Surfaces at the Electron Microscopic Level: A New Method, Theory and Application" in Journal of Histochemistry and Cytochemistry, vol. 25, No. 11, pp. 1187-1200 (1977).

Rita Gupta, et al., "Rapid Antibody Capture Assay for Detection of Group-A Streptococci Using Monoclonal Antibody and Colloidal Gold-Monospecific Polyvalent Antibody Conjugate" in Journal of Immunoassay, 13(3), 441-455 (1992).

* cited by examiner

IMMUNOASSAY SYSTEM

CROSS-REFERENCE TO RELATED APPLICATIONS

The present application is a continuation-in-part of U.S. patent application Ser. No. 09/813,071, filed Mar. 20, 2001, now abandoned entitled IMPROVED IMMUNOASSAY SYSTEM, which was a continuation of U.S. patent application Ser. No. 09/295,847 filed Apr. 21, 1999, now abandoned entitled IMPROVED IMMUNOASSAY SYSTEM, which is a continuation of U.S. patent application Ser. No. 09/195,309 filed on Nov. 18, 1998, now U.S. Pat. No. 6,480,310 entitled IMPROVED IMMUNOASSAY SYSTEM.

STATEMENT RE: FEDERALLY SPONSORED RESEARCH/DEVELOPMENT

Not Applicable

BACKGROUND OF THE INVENTION

The present invention is directed to improved methods and immunoassays for detecting two or more ligands in a liquid sample suspected of containing such ligands, and more particularly, improved methods and immunoassays for rapidly and qualitatively detecting the presence or absence of one or more ligands via a single, rapid, competitive ligand-receptor reaction.

Immunoassays, also referred to as ligand-receptor assays, are well-known in the art. Since their introduction in 1971, immunoassays have been widely utilized in the medical field as a diagnostic tool to detect minute amounts of hormones, drugs, antibodies and other substances suspected of being present in a given fluid sample. Immunoassays have found further application in determining the presence and concentration of ligands in food products and environmental samples.

Such assays rely on the binding of ligands by receptors to determine the concentration of such ligands in a given sample and are typically characterized as either competitive or non-competitive. Non-competitive assays generally utilize receptors in substantial excess over the concentration of ligands to be determined in the assay. Typical of such non-competitive immunoassays include sandwich assays, which detect the presence of a ligand by binding two receptors thereto. In such arrangement, the first antibody is bound to a solid phase such that when the ligand is present, such ligand becomes affixed thereto. A second receptor having a label covalently attached thereto, which may comprise a radioactive, fluorescent, enzymatic, dye or other detectable moiety (collectively referred to as tracers), is introduced to the assay which consequently binds to the bound ligand, to the extent the ligand is present, and thereafter produces a signal consistent with the presence of such ligand. If the sample does not contain the molecules of interest, the labeled antibody is carried past the immobilized antibody without reacting which, as a consequence, will not cause a change in the membrane. Such non-competitive immunoassays are primarily useful for the detection of large molecules such as proteins, large hormones or molecules which have multiple binding sites, such as human chorionic gonadotropin (HCG) and typically will not work with small molecules that have only one binding site.

Competitive assays, in contrast, generally involve competition between a ligand present in a given sample, and a ligand analog having a tracer/label covalently linked thereto to permit detection for a limited number of binding sites provided by the ligand receptor, which typically comprises an antibody bound to a solid phase. Such assays are particularly suited to detect smaller molecules, such as drugs and drug metabolites. In this context, drug analogs are utilized that have been covalently bound to a protein which is then immobilized on a membrane. Antibody specific to the drug is then labeled and immobilized on a porous pad. When a sample is added which is suspected of containing a given analyte, such sample dissolves the labeled antibody and carries it into contact with the immobilized drug-protein region. If there is little or not drug in the sample, a large amount of the labeled antibody is bound to the immobilized drug-protein region which, consequently, produces a detectable signal. If the sample contains a high amount of drug, little or no labeled antibody is bound to the immobilized drug-protein region and thus in turn gives little or no signal.

Early immunoassays required tedious manual steps and long incubation times, typically lasting for several hours. Recent advancements in immunoassays, however, have overcome such deficiencies and can now allow an immunoassay to be formed in less than ten minutes. Such immunoassays may further typically be performed with only one step, which typically comprises mixing all the reactants of a competitive ligand-receptor assay, namely, a fluid sample suspected of containing the ligand, a labeled ligand analog, and a receptor (antibody) bound to a solid phase, with the quantity of ligand being determined by its effect on the extent of binding between the ligand receptor and the labeled ligand analog.

Today, rapid immunoassays generally consist of an adhesive-covered plastic backing onto which several porous pads and a piece of protein-binding membrane are attached. The membrane typically contains a section that has been impregnated with a binding partner (i.e., a receptor or ligand analog). A second pad is typically provided which contains a labeled target molecule or labeled antibody (i.e., tracer) that is placed in direct contact with the protein-binding membrane. When a sample suspected of containing a target ligand is contacted with the immunoassay, such sample dissolves the labeled element or tracer and the capillary action of the protein-binding membrane subsequently draws the sample with tracer dissolved therein into contact with the impregnated binding partner. When this reaction occurs, there is a change in the appearance of the binding membrane, with the difference providing a qualitative and quantitative indication of the presence or absence of the ligand suspected of being present in such sample.

While today's rapid competitive immunoassays are considered generally effective, such assay methods continue to suffer from significant drawbacks. In particular, the reaction between the labeled antibody and the drug in a sample, to the extent present, is known to begin prior to when the labeled antibody reaches the immobilized drug-protein region. Moreover, because the reaction time for such assays is dependent upon variables, such as sample viscosity and membrane porosity, such variability in time allows more or less reaction between the labeled antibody and sample which decreases the sensitivity of the assay and gives rise to inconsistent results.

Accordingly, there is a substantial need in the art for a rapid immunoassay that, in addition to providing a rapid qualitative indication as to whether or not a specific ligand is present within a given sample, has greater sensitivity and reproduceability than prior art assays and methods. Specifically, there is a need for rapid immunoassays and assay methods that can be performed in a single step that further provides qualitative results by utilizing a single competitive assay between a ligand and ligand analog with binding sites to a bound receptor. In addition, there is a need in the art for an immunoassay and assay method that are inexpensive, relatively easy to manufacture, and capable of being utilized for a wide variety of applications. There is still further a need for a rapid, single-step competitive immunoassay that can identify the presence of two or more suspect ligands in a given sample.

BRIEF SUMMARY OF THE INVENTION

The present invention specifically addresses and alleviates the above-identified deficiencies in the art. In this regard, the present invention is directed to a single-step, competitive immunoassay and competitive assay method that are useful in detecting the presence or absence of target ligands in a fluid sample, such as urine, that are more rapid, and have greater reproduceability and sensitivity than prior devices and methods. The systems and methods of the present invention are particularly well suited for detecting the presence of metabolites of certain abused drugs as excreted in the urine, but may further be used to detect certain hormones or other substances, such as tumor markers, for diagnostic purposes.

According to a preferred embodiment, the immunoassay system comprises an elongate strip which has incorporated thereon all of the reagents necessary to perform an immunoassay. Specifically, such strip consists of an adhesive-coated plastic support onto which a piece of protein-binding membrane and first and second absorbent pads are placed. The first pad comprises a high capacity absorbent which serves to absorb a portion of a fluid sample. The second pad contains a freeze-dried colloidal gold tracer onto which is absorbed a novel ligand analog-protein complex that becomes soluble when contacted with the sample. The protein-binding membrane has at least one stripe or zone of antibody applied to it being specific to the ligand of interest (i.e., the presence or absence of the drug sought to be detected), as well as the ligand analog. The first absorbent pad, second absorbent pad and membrane are further preferably sequentially arranged adjacent one another in a generally linear fashion.

The immunoassay further preferably includes at least one second ligand analog protein complex, unrelated to the ligand or ligand analog, that is also absorbed onto the same colloidal gold particles bearing the first ligand and protein complex that are contained within the second absorbent pad, and a second stripe or zone of antibodies formed on the membrane having an affinity to bind the second ligand analog for use as a test control. A third absorbent pad formed adjacent the membrane may also be preferably provided to serve as an additional reservoir for the fluid sample. The immunoassay may further include indicia formed thereon, and preferably upon the first and/or third absorbent pads thereof to facilitate interpretation of the results of the immunoassay.

To utilize the test, the user need only place the immunoassay strip into a fluid sample (i.e., urine) up to a specified level which preferably does not exceed the second absorbent pad containing the ligand analog-protein-colloidal gold complex. The urine is sequentially absorbed by the first and second absorbent pads, which causes the colloidal gold particles with protein-analog absorbed thereon (i.e., tracer) to become rapidly resolubilized. The resultant admixture is then drawn by capillary action into contact with the antibody immobilized on the membrane. To the extent present, the drug/metabolite of interest competes with the tracer to bind with the antibodies bound to the membrane. In this regard, the immunoassay system of the present invention provides for an excess of tracer in all situations such that in the absence of a drug/metabolite sought to be detected, the tracer will necessarily bind to substantially all of the antibody, and thus will produce a visible signal indicative of such absence.

On the other hand, if the sample contains an amount of drug/metabolite above predetermined cut-off levels, such drug/metabolite will necessarily compete with the tracer and thus prevent the latter from binding to the antibodies. As a consequence, a portion of the tracer will be unable to bind to the antibodies and thus no visual signal will be generated thereby. Accordingly, the immunoassay system of the present invention will provide a signal in the absence of the target drug/metabolite sought to be detected, but will not provide such a signal should the same be present.

On average, the test takes approximately ten minutes or less to perform. As discussed above, to ensure accuracy, the immunoassay of the present invention may preferably be provided with a second stripe or zone of control antibodies specific to a second, unrelated tracer or label that is designed to provide a visual indication in every instance, preferably in the form of a control band, where a respective test strip is utilized. In this regard, such control band ensures that the system is functioning properly when the immunoassay indicates the presence of a particular drug/metabolite (i.e., fails to provide a visual indication indicative that no such compound is present). The immunoassay system may further be designed such that tests for multiple metabolites from other frequently abused substances, such as amphetamine, cocaine, marijuana, opiates and PCP, may be incorporated onto a single strip, the presence of which is detected via the use of a single particulate dye having the appropriate corresponding ligand analogs bound thereto. Likewise, it is contemplated that such immunoassay system may be developed to indicate the presence or absence of tumor markers for prostate and bladder cancers, heart attack markers and osteoporosis indicators. It is further envisioned that such immunoassay system can be developed to detect various diseases such as hepatitis, HIV and other types of infectious diseases.

BRIEF DESCRIPTION OF THE DRAWINGS

These, as well as other features of the present invention will become more apparent upon reference to the drawings wherein.

DETAILED DESCRIPTION OF THE INVENTION

The detailed description set forth below in connection with the appended drawings is intended merely as a description of the presently preferred embodiment of the invention, and is not intended to represent the only form in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiments that are also intended to be encompassed within the spirit and scope of the invention.

Figure 1:
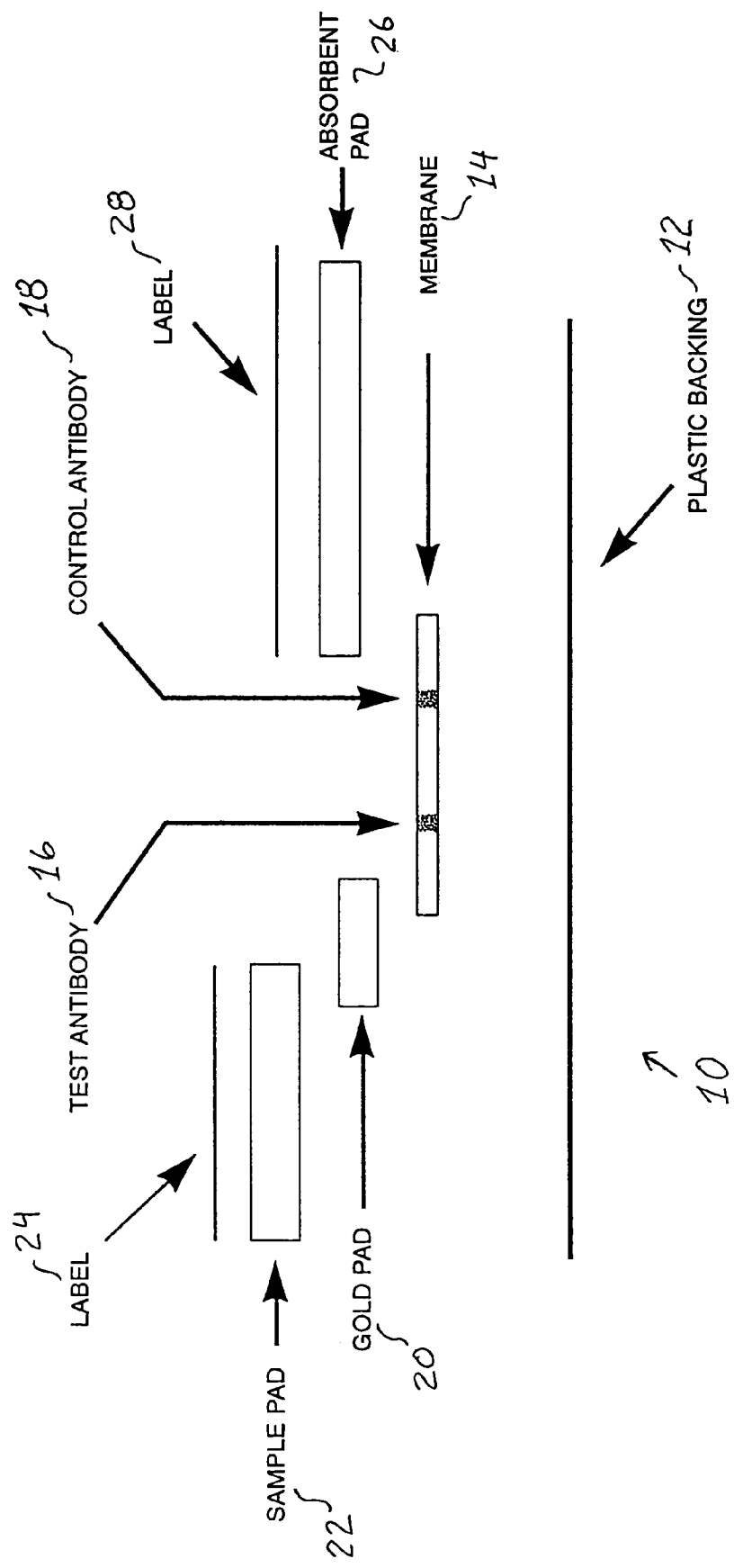
FIG. 1 is an exploded schematic diagram of the components comprising an immunoassay system as constructed in accordance with a preferred embodiment of the present invention.

Referring now to the drawings, and initially to FIG. 1, there is schematically depicted the various components comprising an immunoassay 10 constructed in accordance with a preferred embodiment of the present invention. As illustrated, the immunoassay 10 comprises a plastic backing 12 upon which are formed the various other components necessary to perform an assay, and more particularly, detecting the presence of a ligand suspected of being present in a liquid sample. At the outset, it will be appreciated by those skilled in the art that the term "ligand" may encompass any type of specific analyte or a substance which, if detected, could be used to infer the presence of the analyte in a sample. In this regard, in the context of the present invention, it should be recognized that the term "ligand" includes without limitation, drugs, hormones, antigens, antibodies, haptens, deoxyribonucleic acid (DNA), ribonucleic acid (RNA), any metabolites thereof and any other substances of either natural or synthetic origin which may be of diagnostic interest.

With respect to the various other components utilized to conduct the assay according to the preferred embodiment of the present invention, there is provided a porous membrane 14 upon which are formed a test receptor or antibody 16 having a specific binding affinity for the ligand sought to be detected within the fluid sample. Optionally, there may further be provided a control receptor or antibody 18, likewise formed within a specific zone or striped region upon the membrane 14 having a specific affinity for an unrelated control ligand or reagent having a label bound thereto that, as discussed more fully below, provides a visual indication for purposes of confirming the validity of the assay.

Additionally disposed upon the plastic backing 12 is a second absorbent pad or gold pad 20, the latter being formed adjacent membrane 14 at the proximal end thereof and in closest proximity to the zone or stripe of test antibody 16 formed thereon. Such gold pad 20 essentially comprises a layer of absorbent material within which is distributed a novel ligand analog having a specific affinity for the test antibodies 16 formed upon the membrane 14, discussed more fully below.

Formed adjacent to and proximal such gold pad 20 is a first pad or sample pad 22, the latter comprising a high absorbent material. As will be recognized by those skilled in the art, such sample pad 22 is designed to act as a reservoir such that when a fluid sample is introduced to the device, such sample is absorbed thereby and contacted with the other aforementioned components, namely gold pad 20 and membrane 14, of the immunoassay of the present invention in a sequential, systematic method. In this regard, it will be appreciated that sample pad 22, gold pad 20 and membrane 14 will preferably be formed adjacent one another and aligned in a generally linear fashion such that when the sample pad 22 is contacted with such fluid sample, such fluid sample will be caused to migrate systematically from the sample pad 22 to the gold pad 20 and to the membrane 14. To the extent the same is provided, the fluid sample will further extend to the absorbent pad 26, the latter also being designed to act as a reservoir.

With respect to the preferred formulation of labeled ligand analog or labeled drug dispersed within gold pad 20, such preferably comprises an actual molecule of the ligand itself covalently attached to a protein with the resultant ligand/protein complex being absorbed onto the surface of colloidal gold particles or granules. In an alternative embodiment, such labeled analog may be formed by adhering the protein to the dye (i.e., colloidal gold particles). And thereafter attaching the ligand thereto. In either embodiment, the labeled ligand and analogs comprising the same will be specifically formulated such that when the gold pad 20 comes into contact with the fluid sample, such ligand analog will become soluble and dissolve within the fluid sample.

Along these lines, it is contemplated that more than one ligand/protein complex can readily be absorbed upon the colloidal gold particles to thus enable the presence of two or more substances to be detected via the use of a single particulate dye (i.e., colloidal gold) that can carry two, three, four or five ligand analog protein complexes capable of binding to a corresponding number of different receptors to thus enable the same to be used in detecting dissimilar ligands in a liquid sample.

As will be appreciated by those skilled in the art, colloidal gold is preferable for use as a label or tracer in a practice of the present invention insofar as proteins are known to bind spontaneously to colloidal gold, thus rendering resultant sols that are both hydrophilic and stable in the presence of electrolytes. Moreover, the binding of proteins to gold is practically irreversible, and the proteins usually maintain their biological activities. Such properties, and the high electron density of gold particles, thus make stabilized gold sols convenient and preferred for the practice of the present invention. However, it will be recognized that other similar type materials well known to those skilled in the art having an affinity to absorb proteins and protein complexes.

For purposes of the present invention, it should be expressly recognized that the ligand analog (or ligand analogs) must at all times be present in an amount at least equal to and preferably in excess of the number of binding sites available on the test antibodies. In this regard, such ligand analog must be able to saturate the binding sites provided so that in the case of a negative result, an appropriate signal will be generated in the test antibody zone 16 formed upon the membrane 14. To facilitate interpretation of the results of the immunoassay of the present invention, there may preferably be provided an indicator or label 24, which those skilled in the art will recognize may take a form of any suitable type of indicia, that will direct the user's attention to such test antibody zone 16 so that the results of the assay can be correctly perceived.

While such labeled ligand analog is preferably always present in an excess, however, it will further be recognized that the excess of labeled molecules may be selected such that to the extent ligand is present in a given sample, the presence of such ligand at or above a given threshold concentration will enable the ligand to statistically occupy a certain percentage or range of binding sites on the test antibody such that the resultant visual signal produced or not produced will correspond to such concentration of ligand present.

To validate the results produced by the immunoassay 10 of the present invention, there is further preferably distributed within the second or gold absorbent pad 20, a second labeled ligand or reagent having an affinity for the control antibodies or receptors 18 formed upon the membrane 14. Such labeled reagent, similar to the labeled ligand analog, is specifically formulated to become soluble when contacted with the sample fluid as absorbed by the second or gold pad 20. As a consequence, such labeled molecules will disburse within the sample fluid, and hence contact and bind with the control antibody 18 which thus produces a resultant signal. As will be recognized by those skilled in the art, it will be understood that such labeled molecules will be structurally unrelated to the ligand or ligand analog, and will therefore have no binding affinity for the test receptors 16 formed upon the membrane 14 and will not otherwise interfere with the ability of the ligand, to the extent present, to compete with the ligand analog for binding sites thereat. Similar to indicia or label 24, a second label 28 may be preferably provided, and formed upon the third absorbent pad 26 as shown, to facilitate interpretation of the results produced by the control antibody reaction with such second labeled ligand or reagent.

The second labeled ligand or ligand analog is further preferably formulated similar to the ligand analog utilized to compete with the ligand suspected of being present in the fluid sample. As discussed above, such formulation preferably comprises a molecule of the ligand covalently linked to a protein molecule with the resultant complex being absorbed upon the colloidal gold particles or some other similar type of material well known to those skilled in the art as having an affinity to absorb proteins and protein complexes. Alternatively, the second labeled analog may alternatively be formed by adhering the protein to the colloidal gold particles and thereafter attaching the ligand molecules to the protein bound thereto. Preferably, the second ligand analog protein complex will be absorbed upon the same colloidal gold particles onto which the first ligand analog protein complex is absorbed. Accordingly, there will thus be produced a single tracer capable of binding to two different receptors. To the extent desired, a third, fourth, and fifth ligand analog protein complexes can also adhere to the same colloidal gold particles to which adhere the first and second ligand analog protein complex to thus enable the single tracer to bind to yet a further number of different receptors specific to each respective ligand analog absorbed upon the colloidal gold particles.

Figure 2:
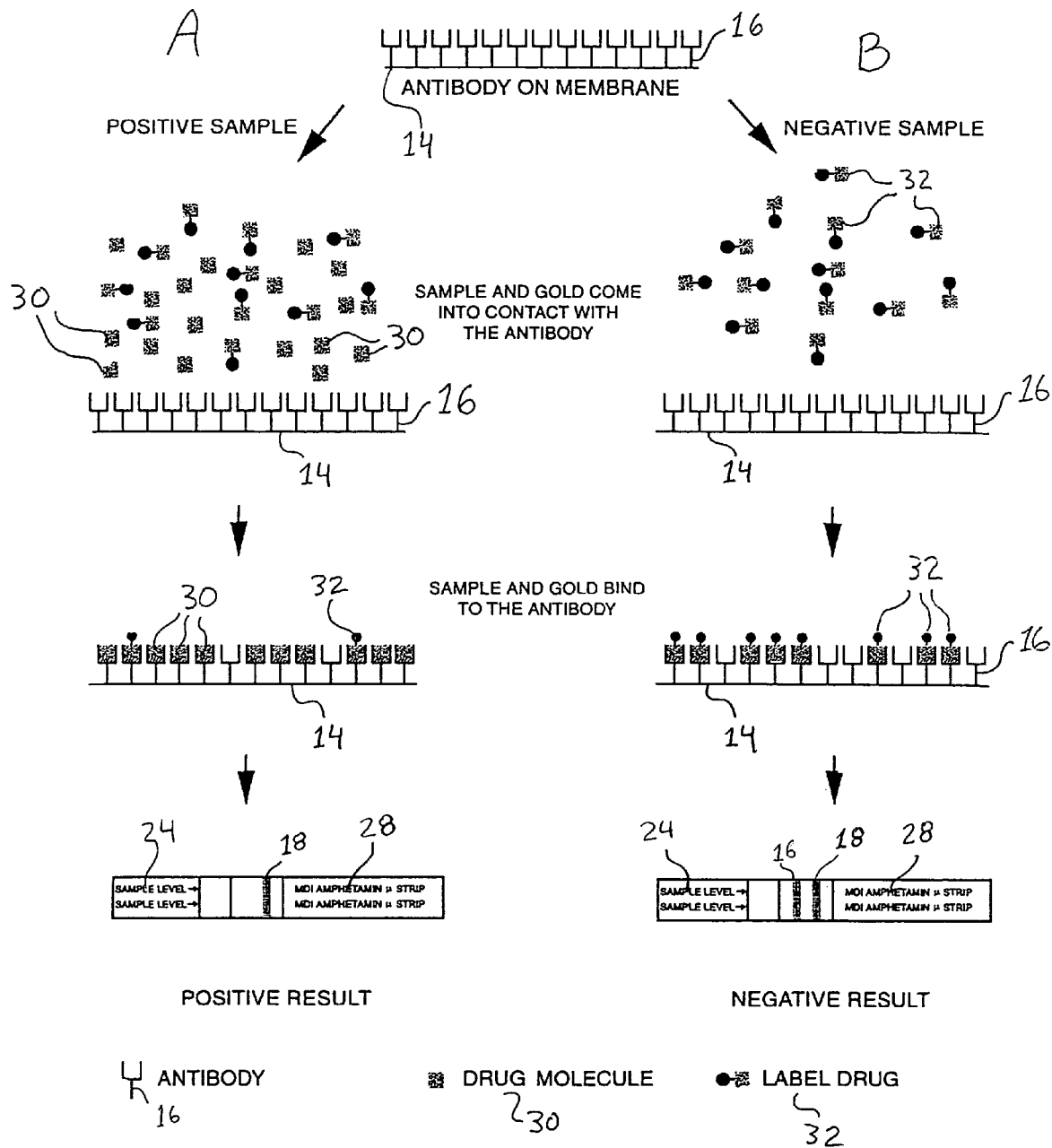
FIG. 2 is a schematic flowchart depicting the operative steps by which the immunoassay system of the present invention detects the presence or absence of a target ligand within a fluid sample.

Referring now to FIG. 2, there is shown the single-step method 30 of the assay of the present invention. As will be recognized, the strip or dipstick embodying the immunoassay of the present invention will initially be contacted with the fluid sample such that the fluid sample will dissolve the labeled ligand analog formed upon the second absorbent pad or gold pad 20. Eventually, the ligand analog and colloidal gold particles will become contacted with the bound test antibodies 16 formed upon the membrane 14.

When so contacted with the fluid sample, either one of two events occur. As represented in Pathway A, to the extent the suspect ligand is present in such fluid sample, as represented by drug molecules 30, such drug molecules 30 will compete with the drug analog molecules, the latter existing as part of an analog-protein complex as absorbed upon the colloidal particles, represented collectively as 32, for binding sites on the test antibodies 16 bound to the membrane 14. To the extent the drug molecules 30 are present in an appreciable amount over a given threshold, a proportionate number of labeled ligand analog molecules 32 will be caused to be displaced such that once all of the binding sites on the test antibodies 16 have become saturated, an insufficient number of labeled ligand analog 32 will be bound thereto such that no visual signal will be produced. With respect to the indication as provided to the user in such cases, only one strip, namely the control strip of antibodies 18 formed upon the membrane, will be visible as shown.

On the other hand, to the extent the fluid sample does not contain any of the suspect ligand, as reflected in Pathway B, the labeled ligand analog 32 will be free to bind with the binding sites on the test antibodies 16 such that the latter become fully saturated therewith. As a consequence, a visually perceptible marker or stripe will appear in the test antibody zone 16 formed on membrane 14, which will thus be indicative of an absence of the target ligand. As will appear insofar as the reaction between unrelated labeled molecules 28 will consequently bind with such control antibodies 18 such that but for a defect in the performance or operation of the assay, a visual indication will always be provided to thus insure the validity of the result concerning the target ligand.

Advantageously, by providing for a one-step competitive reaction, there is thus avoided any potential for a pre-reaction typical of prior art methods whereby labeled antibodies are allowed to react with a ligand in a given sample prior to when such labeled antibody is allowed to react to a bound ligand analog. As such, at no time during the performance of the assay of the present invention is there any possibility that any amount of ligand present in a given sample will become lost or otherwise bind with an unbound binding partner. As a consequence, the sensitivity of the immunoassay and assay method of the present invention will be substantially greater than such prior art methods, and will further provide substantially greater reproduceability to the extent it is necessary to confirm the result of a given assay.

S discussed above, although the present invention has widespread applicability for any of a variety of applications, the immunoassay and assay method of the present invention are particularly well suited for detecting the presence of metabolites of certain abused drugs, and in particular metabolites of opiates, including heroin, codeine and morphine. In such applications, a preferred labeled ligand analog comprises morphine-3-beta-D-glucuronide covalently bound to bovine serum albumin. The resultant morphine-albumin complex is then absorbed onto the surface of colloidal gold particles. As will further be recognized, in such applications the test antibody 16 incorporated into the immunoassay of the present invention will be specific to such metabolite (i.e., the morphine-3-beta-D-glucuronide).

Similarly, the immunoassay and the same method of the present invention can be utilized to detect the presence of amphetamine excreted in the urine by utilizing a test antibody having a binding affinity for amphetamine in combination with a labeled amphetamine, the latter preferably comprising amphetamine covalently bound to bovine serum albumin, the latter being absorbed as a complex onto the surface of colloidal gold particles.

It will further be appreciated that in the practice of the present invention, the ligand analogs and test antibodies used therewith may be selected to have an affinity to one another that is greater or lesser than the affinity of the test antibody for the ligand sought to be detected in the given sample. Moreover, it will be recognized that the number and density of the test antibodies utilized, and more particularly the binding sites thereof, may be selected such that a lack of a visual signal is designed to correspond with a predetermined threshold concentration of ligand in a given sample. For example, it is expressly recognized that the immunoassay and assay method of the present invention may be specifically designed to produce positive or negative results consistent with recognized screening levels, such as those screening levels produced by the United States Substance Abuse and Mental Health Services Administration (SAMHSA). As a particular example, the immunoassay and assay method of the present invention may be specifically designed to produce a positive result (i.e., lack of a visually perceptible signal) to the extent opiate metabolites in a given sample exceed a concentration of 300 nanograms per milliliter of fluid (i.e., urine). Similarly, in the case of amphetamines, a positive result can be designed to coincide with a concentration of 1,000 nanograms of amphetamine metabolites per milliliter of fluid.

With respect to implementation of the immunoassay system and practice of the assay method of the present invention, such process initially comprises the step of collecting the fluid sample, and in particular a urine sample. As per conventional methods, such sample should be collected in glass or non-absorbable plastic containers. To the extent contamination is suspected, such sample should be discarded and another sample collected thereinstead. To the extent the sample is not tested shortly after collection, such sample should be kept refrigerated at a temperature preferably between 2° and 8° C. until such test is conducted. To the extent such sample is not tested within three (3) days, such sample may be frozen at a temperature preferably less than −20° C. for up to twenty (20) days. Thereafter such sample may be thawed and warmed to room temperature before tested. To the extent such sample is turbid, such sample should be centrifuged and the resultant supernatant utilized. The resultant sample must further be thoroughly mixed before testing and must be confined within a pH range of 5-8. To the extent the sample is beyond such range, such pH may be adjusted by using 1M NaOH or 1M HCl to conform the sample to such pH range.

Once properly obtained, the immunoassay strip is contacted with such fluid sample. Preferably, the immunoassay strip is contacted the fluid such that only the sample pad 22 and gold pad 20 are contacted with the fluid sample such that the immunoassay 10 is maintained in an upward configuration extending therefrom, similar to dipstick immunoassay systems. As discussed above, by virtue of the arrangement of sample pad 22, gold par 20 and membrane 14, the fluid sample will be systematically absorbed by the sample pad 22 and then the gold pad 20, which will dissolve the labeled ligand analog.

Due to the capillary attraction of the membrane 14, the fluid sample with label dissolved therein is caused to become saturated therethrough and come in contact with the test antibody immobilized thereon. As discussed above, to the extent present, the suspect ligand in such sample competes with the labeled analog to bind with the antibodies bound to the membrane and, to the extent such ligand is present at or above a threshold concentration, a positive test result, in the form of a lack of a visually perceptible signal at the stripe or zone of test antibody will occur. To the extent the assay is correctly performed, the fluid sample will further dissolve the labeled control ligand or reagent also formed upon gold pad 20 such that the control labeled molecules will bind with the control antibody 18 to produce a visually perceptible signal thereat upon the membrane 14.

Advantageously, such assay only takes on average approximately ten (10) minutes, which is superior than prior art immunoassay systems and methods. Additionally, by virtue of utilizing a novel ligand/protein complex absorbed upon colloidal gold particles, the sensitivity and reproduceability of the results of the immunoassay system and method of the present invention are far superior than those of the prior art. However, it should be expressly recognized that the results from the immunoassay and assay method of the present invention are strictly qualitative and, although such system and method provide for a control reaction to verify the validity of such results, to the extent a positive test result occurs, such positive result should be confirmed via another non-immunological method, such as gas chromatography or mass spectroscopy.

Accordingly, it is understood that the improved system and method described herein and shown in the drawings represents only a presently preferred embodiment of the present invention and that various modifications and additions may be made to such embodiment without departing from the spirit and scope of the invention. As will be recognized, such immunoassay, although preferably constructed as an elongate strip or "dipstick" as it is referred to in the art, may be constructed in any of a variety of formats known now or later developed for use in a given application. Moreover, it should be expressly understood that the immunoassay and assay method of the present invention can be modified such that the same will detect two or more ligands suspected of being present in a given fluid sample. In such embodiment, it will be recognized that two different test antibodies will be provided that will be immobilized on separate and distinct zones of the membrane 14. There will further be provided two separate ligand analogs that, although preferably formed upon a common particulate dye or tracer (i.e., colloidal gold), are designed to bind to either of the two zones or stripes of test antibodies formed upon the membrane. Along these lines, it is contemplated that a multiplicity of dissimilar ligand analogs may adhere to a single particulate dye to thus enable one particulate dye to be utilized to test for a corresponding number of ligands suspected of being present in a given fluid sample. We therefore wish our invention to be defined by the scope of the appended claims as broadly as the prior art will permit, and in view of the specification if need be.

What is claimed is:

1. A dye for use in detecting the presence of two dissimilar first and second ligands in a liquid sample suspected of containing one or both of said ligands via a competitive immunoassay utilizing receptors specific for said first and second ligands comprising:
   a) a particulate dye component;
   b) a first ligand analog covalently bound to a protein;
   c) a second ligand analog covalently bound to a protein, wherein said second ligand analog is dissimilar to the first ligand analog;
   d) wherein said first ligand analog and covalently bound protein and said second ligand analog and covalently bound protein are absorbed upon said particulate dye; and
   e) wherein said particulate dye with both said first and second said ligand analogs absorbed thereon is operative to bind with receptors for both said first and second ligands.

2. The dye of claim 1 wherein said particulate dye comprises colloidal gold granules.

3. The dye of claim 1 wherein the ligand analogs comnrise molecules of the ligands to be detected themselves.

4. The dye of claim 3 wherein said first ligand analog comprises a molecule of morphine-3-beta-D-glucuronide.

5. The dye of claim 3 wherein said second ligand analog comprises a molecule of amphetamine.

6. The dye of claim 1 wherein said particulate dye component comprises a detectable moiety selected from the group consisting of a radioactive compound, a fluorescent compound, an enzymatic compound or particulate metal.

7. The dye of claim 1 further comprising a third ligand analog covalently bound to a protein absorbed upon said particulate dye, said particulate dye with said third ligand analog being further operative to bind with a receptor for said third ligand.

8. The dye of claim 7 further comprising a fourth ligand analog covalently bound to a protein absorbed upon said particulate dye, said particulate dye with said fourth ligand analog being further operative to bind with a receptor for said fourth ligand.

9. The dye of claim 8 further comprising a fifth ligand analog covalently bound to a protein absorbed upon said particulate dye, said particulate dye with said fifth ligand analog being further operative to bind with a receptor for said fifth ligand.

10. The dye of claim 1 wherein said protein comprises bovine serum albumin.

* * * * *